United States Patent [19]

Autio et al.

[11] Patent Number: 4,518,525

[45] Date of Patent: May 21, 1985

[54] METHOD FOR DIVIDING BLOOD HEMOGLOBIN INTO HEME AND GLOBIN

[75] Inventors: Karin Autio; Martti Kiesvaara; Yrjö Mälkki, all of Espoo, Finland

[73] Assignee: Valtion Teknillinen Tutkimuskeskus, Espoo, Finland

[21] Appl. No.: 552,032

[22] PCT Filed: Mar. 11, 1983

[86] PCT No.: PCT/FI83/00022

§ 371 Date: Nov. 3, 1983

§ 102(e) Date: Nov. 3, 1983

[87] PCT Pub. No.: WO83/03198

PCT Pub. Date: Sep. 29, 1983

[30] Foreign Application Priority Data

Mar. 12, 1982 [FI] Finland ................................. 820862
Feb. 22, 1983 [FI] Finland ................................. 830589

[51] Int. Cl.³ ..................... C07C 103/52; C07G 7/00; A61K 35/18; A61K 37/02

[52] U.S. Cl. ...................... 260/112 B; 260/112.5 R; 260/115; 260/245.91; 426/647

[58] Field of Search .................... 260/112 B, 112.5 R, 260/115, 245.91; 426/647

[56] References Cited

U.S. PATENT DOCUMENTS 4,376,727  3/1983  Sato et al. ...................... 260/112 B
4,439,357  3/1984  Bonhard et al. ................ 260/112 B Primary Examiner—Howard E. Schain

[57] ABSTRACT

The invention relates to a method of dividing blood hemoglobin into heme and globin by suspending blood cells, separated from blood, in an acid aqueous solution, by precipitating the heme by means of carboxymethyl cellulose, and by separating the precipitated heme-CMC complex out from the aqueous solution of globin. The obtained heme-CMC complex can be used as such as raw material for the preparation of medicinal iron supplements, and the globin fraction can be used as an additive in fodder or food.

5 Claims, No Drawings

METHOD FOR DIVIDING BLOOD HEMOGLOBIN INTO HEME AND GLOBIN

The present invention relates to a method for dividing blood hemoglobin into heme and globin by suspending blood cells, separated from blood, in an acid solution, in which the gemoglobin is hydrolyzed to heme and globin, by precipitating the heme, and by separating the precipitate from the aqueous solution of globin.

It is known that blood contains iron, and the bulk of this iron is present in the form of iron protoporphyrin in hemoglobin. When the plasma is separated from blood, about 80% of the total proteins contained in the blood remain in the blood cell fraction. The blood cell fraction contains about 38% raw protein, and hemoglobin constitutes about 80% of the dry matter of this raw protein in cows and about 87% in the pigs. Hemoglobin contains about 6% heme, which for its part contains about 9% iron, and the remaining 94% is globin. Interest in organic heme iron had greatly increased, since in certain studies it has been observed to be better absorbed in the intestines than are inorganic iron compounds. Furthermore, certain inorganic iron compounds have been found to have noxious effects. Owing to the strong color, odor and taste of the blood cell fraction and to its perishability, its use as such as a medical iron supplement is out of the question.

Heme has previously been separated from globin on a laboratory scale chromatographically or by extraction, in which case the solvents used have been methylethyl ketone, acetone and dimethyl formamide.

The application of solvent methods on a technological scale results in considerably high solvent costs and solvent regeneration costs.

In addition, the solvents used are highly flammable, and the removal of solvent residues from the final products has proven to be difficult, if the final products are used for fodder, food or medicine.

Swedish Lay-Open Print No. 7 407 882-5 disclosed a method for the separation of heme from globin, a method in which an acid hemoglobin solution is cooled, and a large quantity of ethanol is added to it in two stages in order to precipitate the globin and to separate it by centrifugation. This method also has a disadvantage in that it is necessary to use large quantities of the solvent, which ultimately has to be removed from the final products. In addition, the work has to be carried out at low temperatures, which causes considerable additional expense.

It is previously known to separate the globin of blood from the heme chromatographically with the aid of carboxymethyl cellulose. In this method the hemolyzed and acid hydrolyzed blood cell fraction is directed via an ion exchange column filled with carboxymethyl cellulose, at which time the heme is adsorbed to the carboxymethyl cellulose. However, the amounts of heme which can be separated from globin by this method are so small, that this method is not applicable on a technological production scale.

The object of the present invention is to provide a method for dividing blood hemoglobin into heme and globin, a method in which the above-mentioned disadvantages have been eliminated and in which the final product obtained is a heme-containing product which as such is usable as a raw material for the production of medicinal iron supplements and a globin protein which can be used as an ingredient of food or fodder without the disadvantages caused by solvents.

The main characteristics of the invention are given in accompanying Claim 1.

According to the invention, the blood cell fraction separated from the plasma is hemolyzed by diluting it with water and is acid hydrolyzed by adjusting its pH value to below 3 in order to break the bonds between the globin and the heme. Thereafter the heme is precipitated out from the acid aqueous solution by adding to it an aqueous solution of carboxymethyl cellulose (CMC), and advantageously at such a rate that the weight ratio CMC/globin is at minimum 1:1000, but preferably at maximum 2:10. The iron contained in the heme in this case probably forms a coordinate bond with the carboxyl groups of CMC, which are completely protonized within the pH range used in the invention. The precipitated heme-CMC complex is finally separated from the globin protein solution by means of, for example, centrifugation.

The invention is described below in greater detail with the aid of examples.

EXAMPLE 1

A hemoglobin containing blood cell fraction separated from the plasma is diluted with a water quantity the weight of which is at minimum double the weight of the blood cell fraction, and the pH of the obtained solution is adjusted to so low a value by adding 0.1M HCl that, when an aqueous solution of CMC is added to this solution, the pH of the aqueous solution remains below 3. An aqueous solution of carboxymethyl cellulose is added in such an amount that the weight ratio of carboxymethyl cellulose to globin protein in the aqueous solution is about 1:10. The precipitate produced is separated out from the solution by centrifugation (8000 g, 15 min). The precipitate contains 1.8% iron, and the light-colored solution contains at maximum 0.07% iron as calculated from the weight of the dry matter.

EXAMPLE 2

Hemoglobin containing blood cells separated from blood plasma are slurried in water (weight ratio 1:2). The pH of the solution is adjusted by means of 1M HCl to 1.5, and a quintuple volume of a 0.3% aqueous solution of carboxymethyl cellulose is added to the acid aqueous solution, the weight ratio of CMC to globin protein being 2:10 in the aqueous solution. The mixture is allowed to stand for 15 min, and the precipitated heme-CMC complex is separated out from the globin protein solution, by centrifugation for ½ h (8000 g). The protein fraction contains about 70% of the original globin proteins, and less than 0.05% of its dry matter by weight is iron.

EXAMPLE 3

Blood cells separated from plasma are diluted with water (weight ratio 1:3). The pH of the solution is adjusted by means of 1M HCl to 1.5, and a 0.3% aqueous solution of carboxymethyl cellulose is added at 4 x the volume of the solution, the weight ratio of CMC to globin protein being 1.9:10. The mixture is allowed to stand for 15 min, and the precipitated heme-CMC complex is separated out from the globin protein solution, by centrifugation for 178 h (8000 g). The protein fraction contains about 70% of the original globin proteins by weight, and less than 0.06% by weight of its dry matter is iron.

EXAMPLE 4

Blood cells separated from plasma are diluted with water (weight ratio 1:4). The pH of the solution is adjusted by means of a 1M aqueous solution of hydrochloric acid to 1.5, and a triple volume of a 0.35% aqueous solution of CMC is added, the weight ratio of CMC to globin being 1.7:10 in the aqueous solution. The mixture is allowed to stand for 15 min, and the precipitated heme-CMC complex is separated out from the protein solution, by centrifugation for $\frac{1}{2}$ h (8000 g). The globin protein fraction contains about 80% of the original proteins, and only about 0,07% by weight of its dry matter is iron.

EXAMPLE 5

Blood cells separated from plasma are diluted with water (weight ratio 1:5). The pH of the solution is adjusted by means of a M aqueous solution of hydrochloric acid to 1.4 and a triple volume of a 0.06% aqueous solution of CMC is added (substitution grade at least 1.1) (CMC:protein 1:75). The mixture is allowed to stand for 15 min, and the precipitated heme-CMC complex is separated out from the protein solution by centrifugation. The globin protein fraction contains about 90% of the original proteins and 10% of the original heme fraction.

What is claimed is:

1. A method for separating blood hemoglobin into heme and globin from blood cells comprising separating blood cells from blood plasma, suspending said blood cells in an acidified aqueous medium to disassociate the hemoglobin into heme and globin, adding to said suspension carboxymethylcellulose in an amount sufficient to precipate the heme so disassociated from said hemoglobin, and recovering the resulting precipated heme product.

2. A method according to claim 1, wherein the carboxymethyl cellulose is added to said suspension in such amount that the weight ratio of carboxymethyl cellulose to globin is from about 1 to 1000 to 2 to 10.

3. A method according to claim 1, wherein the carboxymethyl cellulose is added to said suspension in such amount that the weight ratio of carboxymethyl cellulose to globin is from about 1 to 10 to 2 to 10.

4. A method according to claim 1, wherein said carboxymethyl cellulose is added to said suspension in the form of an aqueous solution thereof.

5. A method according to any of claims 1, 3 or 4, wherein the pH of said suspension is maintained at a maximum value of 3 during precipitation of heme.

* * * * *